US011284836B2

(12) United States Patent
Nikolic

(10) Patent No.: US 11,284,836 B2
(45) Date of Patent: Mar. 29, 2022

(54) METHODS AND SYSTEMS FOR IMPROVED PREDICTION OF FLUID RESPONSIVENESS

(71) Applicant: CN MEDICAL RESEARCH LLC, New Orleans, LA (US)

(72) Inventor: Cvetko Nikolic, New Orleans, LA (US)

(73) Assignee: CN MEDICAL RESEARCH LLC, New Orleans, LA (US)

( * ) Notice: Subject to any disclaimer, the term of this patent is extended or adjusted under 35 U.S.C. 154(b) by 383 days.

(21) Appl. No.: 15/221,128

(22) Filed: Jul. 27, 2016

(65) Prior Publication Data
US 2017/0027502 A1 Feb. 2, 2017

Related U.S. Application Data

(60) Provisional application No. 62/197,429, filed on Jul. 27, 2015.

(51) Int. Cl.
*A61B 5/00* (2006.01)
*A61B 5/0205* (2006.01)
(Continued)

(52) U.S. Cl.
CPC .......... *A61B 5/4839* (2013.01); *A61B 5/0205* (2013.01); *A61B 5/02007* (2013.01);
(Continued)

(58) Field of Classification Search
None
See application file for complete search history.

(56) References Cited

U.S. PATENT DOCUMENTS 5,092,340 A * 3/1992 Yamaguchi .......... A61B 5/0432
600/508
5,339,818 A 8/1994 Baker et al.
(Continued)

FOREIGN PATENT DOCUMENTS

WO 2017/100188 6/2017

OTHER PUBLICATIONS

Sbrollini et al. | "Serial electrocardiography to detect newly emerging or aggravating cardiac pathology: a deep-learning approach", BioMedical Engineering Online, Feb. 12, 2019, issue 18, article 15. https://biomedical-engineering-online.biomedcentral.com/articles/10.1186/s12938-019-0630-9.

(Continued)

*Primary Examiner* — Jacqueline Cheng
*Assistant Examiner* — Jairo H Portillo
(74) *Attorney, Agent, or Firm* — Jason P. Mueller; FisherBroyles, LLP

(57) ABSTRACT

The present disclosure provides systems and methods for predicting fluid responsiveness. Embodiments include sensors configured to obtain a high-resolution electrocardiogram signal and a computer system connected to the sensors, the computer system including a memory, a processor, and a display device. Computer system may be configured to receive the electrocardiogram signal from the sensors. Processor may be configured to detect and process changes in at least one of length, amplitude, slope, area, depth, and height of at least one of P, Q, R, S, T, and U complex of the electrocardiogram signal caused by the influence of physiological variables on each other to create a prognostic index. Processor may be further configured to analyze, quantify, and combine the prognostic index of the changes in the electrocardiogram signal and generate a fluid responsiveness (Continued)

prediction. Display device may display the results of the fluid responsiveness prediction.

19 Claims, 2 Drawing Sheets

(51) Int. Cl.
| | |
|---|---|
| *A61B 5/02* | (2006.01) |
| *A61B 5/316* | (2021.01) |
| *A61B 5/349* | (2021.01) |
| *A61B 5/024* | (2006.01) |
| *A61B 5/08* | (2006.01) |
| *A61B 5/0245* | (2006.01) |
| *G16H 50/30* | (2018.01) |
| *A61B 5/333* | (2021.01) |
| *A61B 5/366* | (2021.01) |

(52) U.S. Cl.
CPC .............. *A61B 5/316* (2021.01); *A61B 5/349* (2021.01); *A61B 5/7275* (2013.01); *A61B 5/024* (2013.01); *A61B 5/0245* (2013.01); *A61B 5/08* (2013.01); *A61B 5/333* (2021.01); *A61B 5/366* (2021.01); *A61B 2505/03* (2013.01); *A61B 2505/05* (2013.01); *G16H 50/30* (2018.01)

(56) References Cited

U.S. PATENT DOCUMENTS

| | | | |
|---|---|---|---|
| 7,422,562 B2 | 9/2008 | Hatib et al. | |
| 7,539,535 B1* | 5/2009 | Schlegel | ................ A61B 5/044 |
| | | | 600/509 |
| 8,265,739 B1* | 9/2012 | Boileau | ................ A61B 5/0452 |
| | | | 600/516 |
| 8,617,135 B2 | 12/2013 | Rinehart et al. | |
| 8,790,272 B2 | 7/2014 | Sackner et al. | |
| 2005/0004481 A1* | 1/2005 | Xue | ....................... A61B 5/349 |
| | | | 600/509 |
| 2010/0324827 A1 | 12/2010 | Addison et al. | |
| 2011/0270111 A1* | 11/2011 | Cannesson | ........... A61B 5/0456 |
| | | | 600/521 |
| 2012/0035442 A1* | 2/2012 | Barman | ............. A61B 5/14532 |
| | | | 600/316 |
| 2012/0179007 A1* | 7/2012 | Rinehart | .............. A61B 5/4833 |
| | | | 600/301 |
| 2012/0179011 A1* | 7/2012 | Moon | .................. A61B 5/7207 |
| | | | 600/324 |
| 2012/0310050 A1 | 12/2012 | Osorio | |
| 2013/0053664 A1 | 2/2013 | Jian et al. | |
| 2013/0085357 A1 | 4/2013 | Huber et al. | |
| 2014/0012148 A1* | 1/2014 | Amit | .................. A61B 5/04014 |
| | | | 600/509 |
| 2014/0058229 A1 | 2/2014 | Su et al. | |
| 2014/0187992 A1 | 7/2014 | Wilmering | |
| 2014/0213862 A1 | 7/2014 | Addison et al. | |
| 2014/0316278 A1 | 10/2014 | Addison et al. | |
| 2015/0257690 A1* | 9/2015 | Su | ...................... A61B 5/14552 |
| | | | 600/324 |
| 2017/0112401 A1 | 4/2017 | Rapin et al. | |

OTHER PUBLICATIONS

Matthews et al., "A novel application of deep learning for single-lead ECG classification", Computers in Biology and Medicine, New York, US, Co. 99, Jun. 4, 2018, pp. 53-62.

Zheng et al., "ECG Based Identification by Deep Learning", Oct. 20, 2017, International Conference on Financial Cryptography and Data Security; Springer, Berlin, Heidelberg, pp. 503-510.

* cited by examiner

METHODS AND SYSTEMS FOR IMPROVED PREDICTION OF FLUID RESPONSIVENESS

This application claims the benefit of U.S. Provisional Patent Application No. 62/197,429, filed Jul. 27, 2015, which is incorporated herein by reference.

DESCRIPTION OF EMBODIMENTS

Figure 1:
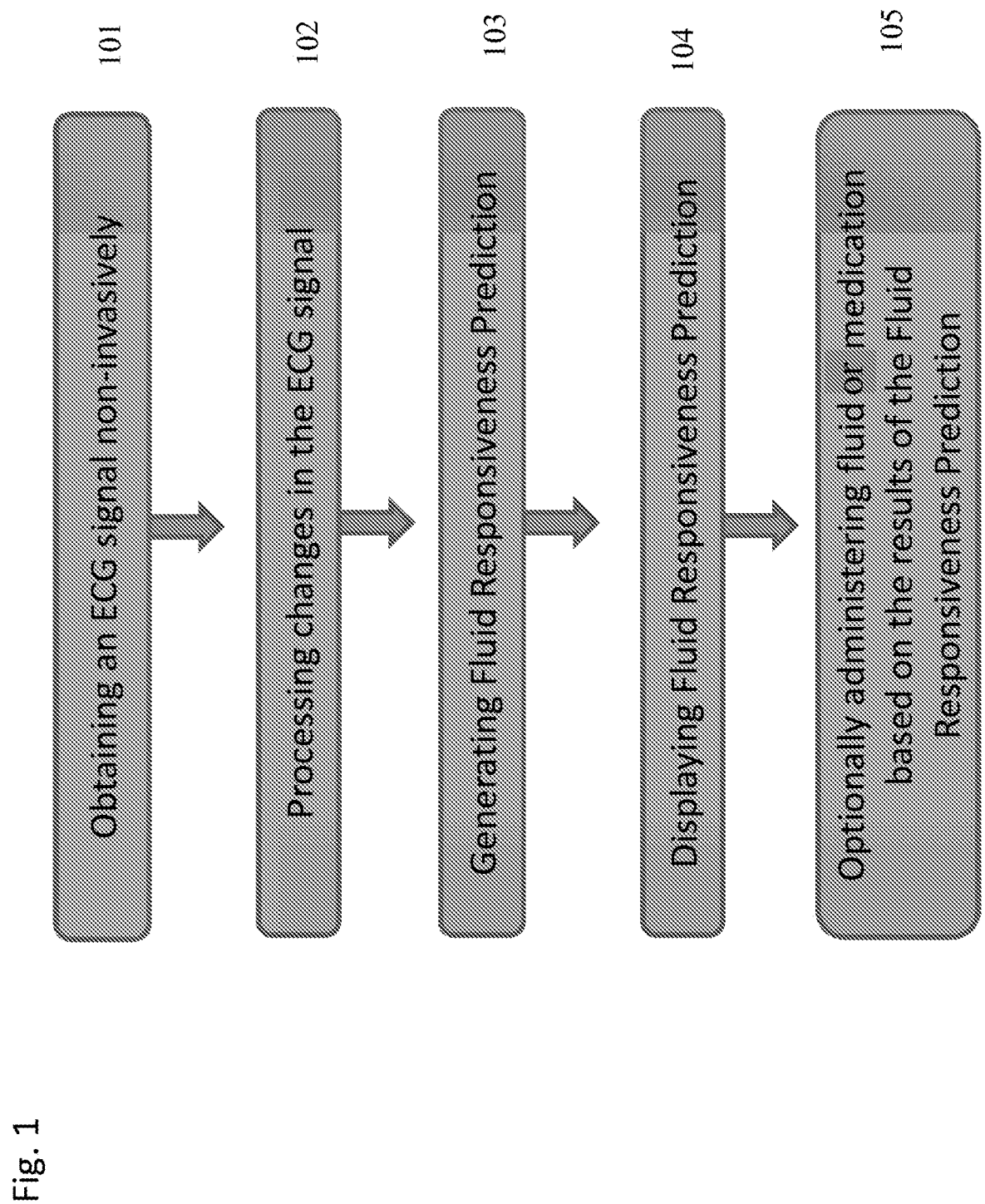
FIG. 1 is a flow chart of a method of predicting fluid responsiveness of a patient using an ECG signal, according to an exemplary embodiment of the present disclosure.

An important issue for physicians in the treatment of patients that are receiving anesthesia during surgery or that are critically ill or unresponsive to interventions is determining how much, if any, intravenous fluid or blood should be administered to the patient in order to maintain optimal cardiac output. Indeed, determining the best and correct course of fluid therapy for a patient is very difficult and clinicians have very few clinical signs to direct them on the right path.

Fluid administration in a hemodynamically unstable patient constitutes a major challenge when it comes to measuring hemodynamic parameters in real time. Accurate clinical assessment of hypovolemia (a state of decreased blood volume) is difficult, as is the decision to undertake fluid resuscitation as the initial treatment strategy. Specifically, predicting whether a hemodynamically unstable patient will positively respond to fluid therapy with an increase in stroke volume and cardiac output is very difficult. On one hand, an insufficient supply of fluid or blood volume can cause a suboptimal (i.e., reduced) cardiac output, which will in turn lead to hypoperfusion, insufficient tissue perfusion, and eventually, organ failure and/0r dysfunction. On the other hand, recent studies have shown that an oversupply of fluid or blood volume may also lead to pulmonary or cardiac failure, extended ventilation time, and/or disruption of the endothelial layer of the vascular system with consecutive blood clotting and passage of fluid into the interstitium (edema). Further, an increased supply of fluid or blood volume does not provide any benefit to patients with decreased heart frequency or contractility; instead, these patients may need heart muscle strengthening medication (such as catecholamines, adrenaline, or their derivatives). A patient's "fluid responsiveness" is thus considered the most important determinant to assess the adequacy of fluid administration and in ensuring optimal cardiac performance and organ perfusion.

Therefore, under conditions of physiological compromise, it has become extremely important to adjust the fluid supply to the exact level required to keep the heart functioning in its optimal range of operation [stroke volume× heart frequency/minute=cardiac output]. Further, the heart's response to this fluid supply, i.e., the heart's "fluid responsiveness", must be continuously monitored to maintain heart function within optimal ranges.

Treatment of the anaesthetized or critically ill patient requires an accurate assessment of the patient's intravascular volume status ("cardiac preload") and the likelihood that the patient will respond (through increased "stroke volume") to a fluid challenge ("fluid responsiveness"). Stroke volume is the amount of blood ejected by the left ventricle of the heart in one contraction. The left ventricle of the heart fills with blood until contraction during diastole (also known as the end diastolic volume, or EDV). The contraction occurs during systole, and some blood is left in the ventricle after contraction (also known as the end systolic volume, or ESV). Stroke volume is then calculated as the difference of ESV from EDV. Stroke volume is then divided by EDV to determine the ejection fraction, or EF. Typical ranges of EF in healthy subjects are between 55-70%. Stroke volume is also affected by preload and afterload. Preload is the load, or stretch, put on the ventricle by the amount of entering blood volume. As preload increases, it increases the strength of the contraction, thus increasing the stroke volume. The afterload is the resistance the ventricle must pump against to eject the stroke volume.

The primary reason to give a patient a fluid challenge is to increase the stroke volume (fluid responsiveness). If the fluid challenge does not increase the stroke volume, volume loading serves the patient no useful benefit (and in fact may be harmful). According to the Frank-Starling principle, as the preload increases, left ventricular (LV) stroke volume increases until the optimal preload is achieved at which point the stroke volume remains relatively constant. In normal physiologic conditions, both ventricles should operate on the ascending portion of the Frank-Starling curve. In most people, an increase in preload (with volume challenge) will result in a significant increase in stroke volume.

A number of methods and techniques have been developed to predict whether and how much fluid should be administered or supplied to a patient in order to maintain optimal heart operation. A method that has been demonstrated to be a useful predictor of fluid responsiveness is the use of Stroke Volume Variations ("SVV"), which are variations observed in the left ventricular stroke volume that result from the interaction of the cardiovascular system and the lungs under mechanical ventilation. SVVs are caused by the cyclic increases and decreases in the intrathoracic pressure due to mechanical ventilation, which lead to variations in the cardiac preload and afterload. Another method that has been demonstrated to be a useful predictor of fluid responsiveness is the use of Pulse Pressure Variations (PPV), which are respiratory variations in arterial blood pressure. However, both of these methods have several disadvantages, including that they require at least some level of invasiveness (e.g. arterial line to assess blood pressure)—a drawback because the general trend in this field has been towards less invasiveness, i.e., providing interventions and monitoring to patients correlating to the sensitivity of their state. For example, patients who undergo fluid increases (for example, ICU patients) are typically in a sensitive state, and so should receive treatment that is less invasive compared to a relatively healthier patient. Specifically, an increased intrathoracic pressure like in the case of mechanical ventilation (for example, during anesthesia or in the ICU) can obstruct the backflow of blood to the heart (for a couple of heartbeats). This effect may be even more pronounced when a higher pressure is applied to a patient with poor blood circulation (potentially causing demasking/hypovolemia).

Further, current methods for predicting "fluid responsiveness" involve a single parameter based on: the derivative of the pulse curve from an arterial measurement, the direct measurement of the stroke volume (surface area integral), or measurement of the blood flow velocity in the AoK (DOPPLER Principle). However, these methods have several disadvantages, including that they are not sufficiently accurate because they are based on a single parameter and do not necessarily account for the different changes caused by the influence of physiologic variables on each other. Additionally, these currently known methods for determination of the "fluid responsiveness" parameter are almost all derivatives of blood flow.

Methods and systems are provided for fluid responsiveness, and, in particular though non-limiting embodiments, methods and systems are provided for predicting fluid responsiveness using an electrocardiogram signal to maintain optimal cardiac output. Embodiments of the present disclosure predict fluid responsiveness using the value of an electrocardiogram (ECG or EKG) signal alone and perform this function at higher ECG sampling rates. Importantly, the present disclosure is completely non-invasive and does not disturb the patient in any way because its function derives from the standard functional analysis of an ECG signal. ECG is a graphical representation of the electric potentials generated by the heart. It is a non-invasive and continuous monitoring method providing information from which the heart rate, underlying rhythm, activity of the atria, and the ventricles can be read in the form of an electrical signal. Such electrical signals are recorded via ECG leads placed on the surface of a body. The ECG has been exclusively used until this point as a monitoring process to monitor heart frequency and arrhythmias in anesthesiology and intensive care medicine.

An exemplary embodiment of the present disclosure predicts fluid responsiveness by using continuous, higher resolution ECGs (e.g., 250 Hz to 1000 Hz) to detect changes in fluid responsiveness parameters. Unlike standard ECGs at 50 Hz, a higher resolution ECG can detect very low amplitude signals in the ventricles (called "Late Potentials") of patients with abnormal heart conditions.

Embodiments of the present disclosure are also not based on a single parameter, but on an algorithm based on changes in an ECG signal caused by the influence of multiple physiologic variables (heart rate, breathing, vascular tone, etc.) on each other—thus providing the necessary accuracy not possible from analyzing a single parameter.

The present disclosure provides systems and methods for predicting fluid responsiveness using a cardiac parameter from an ECG signal to maintain optimal cardiac output. Specifically, the disclosed embodiments present a method for predicting fluid responsiveness by using continuous, higher resolution ECGs (ranging from 250 Hz to preferably 1000 Hz) to detect and process changes in fluid responsiveness parameters based on the ECG signals and generate a fluid responsiveness prediction based on those changes. In alternative embodiments, fluid responsiveness may be predicted using non-continuous or partially continuous higher resolution ECGs.

In an embodiment of the present disclosure, at least two sensors may be provided to obtain an ECG signal non-invasively. The ECG signal may be passed from the sensors to a computer system by various methods, including via an electronic output file. A processor within the computer system may be configured to detect and process changes in the ECG signal fluid responsiveness parameters (i.e. direct alterations of the ECG curves). Once these changes in the ECG signal are processed, the processor may execute a mathematical algorithm stored within a memory of the computer system to analyze and quantify the changes in the ECG signal and generate a fluid responsiveness prediction. A display device may also be provided to display the results of the fluid responsiveness prediction.

According to exemplary embodiments of the present disclosure, methods are provided for predicting fluid responsiveness of a patient using an ECG signal. A method includes obtaining the ECG signal non-invasively using a sensor. The method includes processing changes in the ECG signal fluid responsiveness parameters (i.e. direct alterations of the ECG curves) using a computer system. The method includes quantifying these changes in fluid responsiveness parameters and generating a fluid responsiveness prediction of a patient using a mathematical algorithm embodied within the computer system. The method includes displaying the results of this fluid responsiveness prediction to a physician or other health care provider using a display device. The method may also include a physician or other health care provider using his or her medical expertise and evaluating the results of this fluid responsiveness prediction and determining the next appropriate medical course of action for the patient. This next medical course of action may include, but is not limited to, administering fluid or medication to the patient, performing other medically appropriate steps as necessary based on the results of the fluid responsiveness prediction, or do nothing at all, if medically appropriate.

FIG. 1 illustrates of a method of predicting fluid responsiveness of a patient using an ECG signal to maintain optimal cardiac output of the patient, according to an exemplary embodiment of the present disclosure. The first step may include obtaining an ECG signal from a patient non-invasively 101. The second step may include processing changes in the ECG signal 102. The third step may include generating a fluid responsiveness prediction 103. The fourth step may include displaying the fluid responsiveness prediction 104 to a physician or other health care provider. Finally, the optional fifth step may include administrating fluid or medication based on the results of the fluid responsiveness prediction 105. Although embodiments of the present disclosure describe methods of predicting fluid responsiveness using an ECG signal, alternative embodiments may use any recordable physiological (electrical) signal, including for e.g. Electromyogram (EMG) signals, Electroencephalogram (EEG) signals, etc.

Figure 2:
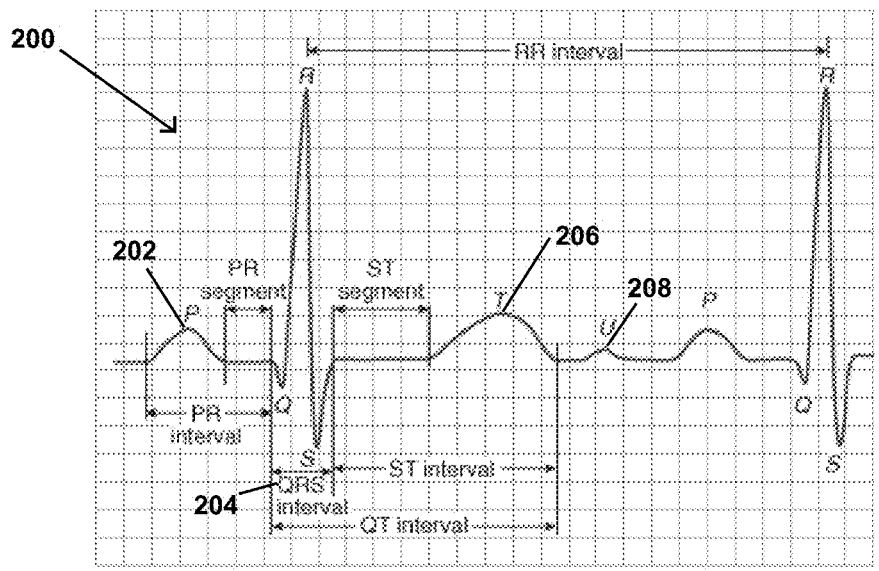
FIG. 2 illustrates a typical ECG signal over a time interval.

FIG. 2 illustrates a typical ECG signal 200 over a time interval. Electrocardiography represents a transthoracic (across the thorax or chest) measurement of electrical activity of the heart over a period of time, as detected by electrodes attached to the outer surface of the skin and recorded by a device external to the body. The recording produced by the noninvasive procedure is termed EKG or ECG. An ECG is used to measure the rate and regularity of heartbeats, as well as the size and position of the chambers, the presence of any damage to the heart, and the effects of drugs or devices used to regulate the heart, such as a pacemaker.

In FIG. 2, an ECG signal 200 is shown. The ECG signal 200 includes a P wave 202, a QRS complex 204, a T wave 206, and a U wave 208. The P wave 202 indicates atrial depolarization, or contraction of the atrium. The QRS complex 204 indicates ventricular depolarization, or contraction of the ventricles. The T wave 206 indicates ventricular repolarization. The U wave 208 typically follows the T wave 206 and may not always be seen. U wave 208 may indicate repolarization of the papillary muscles or Purkinje fibers. The size of the U wave 208 is inversely proportional to the heart rate; as the U wave 208 grows bigger, the heart rate slows down.

Turning back to FIG. 1, each step of the method of predicting fluid responsiveness of a patient will now be addressed in turn. Referring to the first step of obtaining an ECG signal from a patient non-invasively 101, the term non-invasively indicates that no artificial methods are used during the recording of the ECG signal to create an increased intrathoracic pressure. Artificial methods may include any measurements that may for e.g. puncture the surface of a patient's skin to obtain an ECG signal. Artificial methods do not include for e.g. mechanical ventilation or leg raising of a patient that may be performed to improve the quality of the measurements being obtained. In some embodiments, the ECG signal may be obtained from at least two sensors coupled to a patient. A sensor may be a device capable of generating continuous, high-resolution ECG data (e.g., 250 Hz to 1000 Hz). Examples of such devices include commercially available ECG setups from GE Healthcare® Inc. In an alternative embodiment of the present disclosure, the ECG signal may be passed from the sensors to a storage device, whereby the ECG signal may be obtained from the storage device. A storage device may be an apparatus capable of providing continuous, high-resolution ECG data (e.g., 250 Hz to 1000 Hz). Embodiments of the storage device include a flash memory or hard disk drive. Exemplary embodiments of the present disclosure may use continuous, high-resolution ECGs (ranging from at least 250 Hz to preferably 1000 Hz) to facilitate the fluid responsiveness prediction. Although the disclosed embodiments refer to a sensor and storage device, the ECG signal may be acquired from other known types of ECG acquisition hardware.

In an embodiment of the present disclosure, the ECG signal may be passed from the sensors or the storage device to a computer system. Passing the ECG signal to the computer system may be done in various ways, including via an electronic output file (and/or related ECG acquisition hardware). In exemplary embodiments, the computer system may be a device, apparatus, and system capable of processing continuous, high-resolution ECG data (e.g., 250 Hz to 1000 Hz). Embodiments of the computer system include commercially available desktop computer systems such as a PowerMac®. The computer system may include a general-purpose control unit, such as a processor or microprocessor connected to an internal bus, data acquisition, data storage, and/or input/output devices including a display device and printer. The processor or microprocessor may be configured to execute software, which may include an operating system and one or more applications, as part of performing the functions described herein. A read-only memory (ROM), a random access memory (RAM), user inputs, and a display device may also be operatively connected to the bus.

The RAM and the ROM are illustrated by way of example, and not limitation. Any suitable computer-readable media may be used in the system for data storage. Computer-readable media are configured to store information that may be interpreted by the microprocessor. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

Referring now to the second step of processing changes in the ECG signal 102, a processor within the computer system may detect, analyze, and process changes in the fluid responsiveness parameters (i.e., direct alterations of the ECG curves) to create a prognostic index. Particularly, the processor may be configured to detect and process changes in at least one of the length, amplitude, slope, area, depth, and height of at least one of the P, Q, R, S, T, and U complex (see FIG. 2) of the ECG signal caused by the influence of various physiological variables on each other to create the prognostic index. This prognostic index may be based on processed changes in the ECG signal fluid responsiveness parameters caused by the influence of at least two or more physiological variables on each other such as heart rate, breathing, and/or vascular tone. The changes in the ECG signal may be detected in volume depleted patients comparing ECG periods during the end of inflation of a ventilator hub and during the end of the exhalation period (i.e., during periods of differing intrathoracic pressures). An alternative embodiment of the present disclosure may involve the use of methods and systems of the present disclosure in spontaneous breathing patients.

Specifically, the prognostic index (and subsequently generated fluid responsiveness prediction) may be based on several relative changes in at least one of the P, Q, R, S, T, and U complexes of the ECG curve, including, but not limited to, at least one of the absolute length of the P wave/10-25%, the absolute amplitude of the P wave/10-30%, the slope of the P wave/5-25%, the area under the curve of the P wave/10-30%, the PQ segment/15-35%, the absolute length of the QRS complex, the slope of the decrease from isoelectric to the Q point, the slope of the increase towards the R point, the absolute depth of the Q point, the absolute height of the R point, the area under the curve of the QRS complex, the absolute length of the ST segment, the absolute length of the ST segment including the T wave, the absolute length of the ST segment including the U wave, the distance from the beginning of the P wave and the top of the P wave to the top of R, the slope of the distance from the beginning of the P wave and the top of the P wave to the top of R, the distance from the top of R to the end of the T wave, the slope of the distance from the top of R to the end of the T wave, and/or the area under the triangle built of both the distance from the beginning of the P wave and the top of the P wave to the top of R, as well as its corresponding slope, with an isoelectric line. See, e.g., FIG. 2. In some embodiments, if more than one ECG signals are used, the fluid responsiveness prediction may be based on the change in vector, change of a heart's electrical axis of the respective ECG leads. All of these changes in the P, Q, R, S, and T complexes of the ECG curve may be observed in fluid responsive patients in a digital overlay of ECG curves comparing a curve during end of inflation (ventilator hub) to end of exhalation. Further, all of these changes may be within a range of 10-30%—the more volume depleted (fluid responsive) a patient is, the higher the difference in his or her corresponding intra-thoracic pressure.

The above referenced changes in the P, Q, R, S, T, and U complexes of the ECG curve does not have to be observed in one patient; in fact, the more these changes are observed and compared in several individual patients during ventilation and the more pronounced they are, the more certain the fluid responsiveness prediction. In various embodiments, the prognostic index may include data derived from observations and comparisons of changes in multiple patients. Particularly, the larger the number of empirical data points present, i.e. the larger the number of patients evaluated, the more comparative data may be obtained. Further, the longer the empirical data points are recorded/collected from individual patients, the more comparative data may be obtained. In some embodiments, the prognostic index may therefore include both existing data collected based on changes in the P, Q, R, S, T, and U complexes of high-resolution ECG signals in multiple patients, and/or newly collected data based on the same changes from an individual patient. The existing data may act as a baseline to which the newly collected data may be compared. In other embodiments, the prognostic index may only include newly collected data from an individual patient. In this embodiment, varying information within the newly collected data may be analyzed and compared to each other. Therefore, embodiments of the present method may include using a high-resolution ECG device to generate a prognosis based on comparing changes in at least one of the P, Q, R, S, T, and U complexes of high-resolution ECG signals relative to a pre-determined prognostic index based on data collected from multiple patients, or relative to each other based on data collected from an individual patient.

Embodiments of the present disclosure may employ various methods for detecting, analyzing, and processing the changes in at least one of the P, Q, R, S, T, and U complexes of multiple ECG signals. In an exemplary embodiment, this analysis may be based on a mathematical integration known as the "Simpson's rule" or modifications thereof such as, e.g., the "Composite Simpson's rule." In numerical analysis, the Simpson's rule is a method for numerical integration, the numerical approximation of definite integrals. If the function being integrated is relatively smooth over a time interval, the Simpson's rule may be used to obtain an adequate estimated approximation of underlying data to the exact integral. However, when trying to integrate numerical data that is not smooth over a time interval (as may be the case for the data in the prognostic index described herein), the Simpson's rule may not be as accurate. However, by breaking up the interval into a number of small subintervals, the Simpson's rule may then be applied to each subinterval, with the results being summed to produce an approximation for the integral over the entire interval. In particular embodiments, this modified application of the Simpson's rule (i.e., the Composite Simpson's rule) may therefore be used to perform analysis and quantification of the data in the prognostic index. In alternative embodiments, other suitable methods of analysis may be used to analyze the data in the prognostic index.

Referring now to the third step of generating a fluid responsiveness prediction 103, the processor may execute a mathematical algorithm stored within a memory of the computer system to analyze, quantify, and combine the prognostic index of the changes in the ECG signal and generate a fluid responsiveness prediction based on numerical data in the prognostic index. Particularly, the fluid responsiveness prediction may be obtained based on an analysis and comparison of existing and newly collected data in the prognostic index. In some embodiments, the fluid responsiveness prediction may be generated by analyzing and comparing data obtained from one data set (i.e. from one patient being evaluated) to an established data set in the prognostic index (i.e. from multiple patients). In alternative embodiments, the fluid responsiveness prediction may be generated by analyzing and comparing changes in fluid responsiveness in an individual patient. For example, in an embodiment, data being collected from a patient may indicate certain ECG curves with relatively higher "spikes"/ "peaks" than other ECG curves of the same patient or other patients based on existing data in the index. These spikes may be evaluated and characterized as numerical data via the methods of analysis described herein. A fluid responsiveness prediction comparing the newly collected and existing data may then be generated and displayed in various forms, including but not limited to as a table, listing, chart, and/or other suitable visual depictions such as a digital overlay of ECG curves.

Referring now to the fourth step of displaying the fluid responsiveness prediction 104 to a healthcare provider or other authorized person, the generated fluid responsiveness prediction may be displayed on a display device communicatively coupled to the computer system. The display device may be a cathode ray tube display, a flat panel display, such as a liquid crystal display (LCD), a light-emitting diode (LED) display, a plasma display, or other type of monitor. Embodiments of the display device include commercially available monitors, such as an Apple Thunderbolt Display. It will be understood that other suitable metrics may be displayed to indicate levels of fluid responsiveness, such as by a status bar, a visual alarm, an audible alarm, any other suitable indication, or combinations thereof. The level of fluid responsiveness may also be outputted to suitable output devices, such as a computer, a computer-readable medium, a printer, or combinations thereof.

An exemplary embodiment of the disclosure may further include the optional fifth step whereby a physician or other health care provider may review the results of the generated fluid response prediction on the display device and make the medical determination to administer fluid to a patient 105. An alternative exemplary embodiment of the disclosure may include the optional fifth step whereby the physician or other health care provider reviews the results of the generated fluid response prediction on the display device and instead makes the determination to administer medication to the patient 105. This scenario will likely arise in a case where an increased supply of fluid or blood volume may not provide any benefit to a patient with decreased heart frequency or contractility; instead, the patient may need heart muscle strengthening medication (such as catecholamines, adrenaline, or their derivatives).

An alternative exemplary embodiment of the disclosure may include the optional fifth step whereby the physician or other health care provider may review the results of the generated fluid response prediction on the display device and instead make the determination, based on his or her expertise, to follow another medically appropriate course of action for the patient 105. Yet another exemplary embodiment of the disclosure may include a scenario whereby the health care provider or other authorized person may review the results of the generated fluid response prediction on the display device and come to the conclusion that the patient does not need any additional medical treatment at all 105.

In one exemplary but non-limiting embodiment, a hemodynamically unstable patient's fluid responsiveness may be obtained by the following method. At least two sensors described herein may first be coupled to the patient and used to obtain the patient's ECG signal. See, e.g., FIG. 2. The ECG signal may be passed from the sensors to a computer system described herein. A processor within the computer system may then detect, analyze, and process changes in at least one of the length, amplitude, slope, area, depth, and height of at least one of the P, Q, R, S, T, and U complex of the ECG signal caused by the influence of the patient's various physiological variables on each other to create a prognostic index described herein. In various embodiments, the patient's ECG signal may indicate some curves with a higher "spike"/"peak" than other curves. In some embodiments, the processor may for e.g. analyze and compare the area under the curve of the QRS complex of the "spiked" curve with the area under the curve of the QRS complex in another non-spiked curve. This calculation and analysis of the area under the curves of the spiked and non-spiked QRS complexes may be performed using the Composite Simpson's rule described herein. Once this data is obtained and stored in the prognostic index, the processor may then generate a fluid responsiveness prediction based on this data. In this particular embodiment, the prognostic index may only include relevant newly collected data from this patient being evaluated. For example, the relevant data from the spiked curve may be processed and compared to the data from the non-spiked curve and displayed in a suitable viewable format, e.g., a comparative chart. In other embodiments, the prognostic index may include relevant newly collected data from both the patient being evaluated as well as baseline data from multiple patients for comparison to the newly collected data. A physician viewing this comparative chart may then make the medical determination to either administer fluid or medication, follow an entirely different medically appropriate course of action, or not take any further action.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar systems for loading computer programs or other instructions into the computer or processor.

The term computer or module may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term computer.

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The terms software and firmware are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted.

What is claimed is:

1. A system for predicting fluid responsiveness, comprising:
   at least two sensors configured to continuously obtain a high-resolution electrocardiogram signal at a frequency of greater than 250 Hz to about 1000 Hz; and
   a computer system connected to the at least two sensors, the computer system including a memory, a processor, and a display device,
   wherein the computer system is configured to receive the high resolution electrocardiogram signal at the frequency of greater than 250 Hz to about 1000 Hz from the at least two sensors as continuous high-resolution electrocardiogram data,
   wherein the processor is configured to use real-time processing to detect, analyze, and process changes within a range of 10 to 30% in at least one of length, amplitude, slope, area, depth, and height of one or more of P, Q, R, S, T, and U complexes of the electrocardiogram signal, including determining changes in an area under the curve of the QRS complex, and a change in the rise angle of the QRS complex, caused by the influence of physiological variables on each other to create a prognostic index,
   wherein the processor analyzes, quantifies, and combines the prognostic index of the changes in the electrocardiogram signal to generate a fluid responsiveness prediction based on real-time processing to continuously update the fluid responsiveness prediction, and
   wherein the display device is configured to continuously display the fluid responsiveness prediction.

2. The system of claim 1, wherein the prognostic index is based on at least two physiological variables.

3. The system of claim 2, wherein the physiological variables include at least two of heart rate, breathing, and vascular tone.

4. The system of claim 1, wherein the prognostic index depends on at least one of: changes in the absolute length of the P complex in a range of 10-25%, changes in the absolute amplitude of the P complex in a range of 10-30%, changes in the slope of the P complex in a range of 5-25%, changes in the area under the curve of the P complex in a range of 10-30%, changes in the PQ complex in a range of 15-35%, changes in the absolute length of the QRS complex, changes in the slope of the decrease from isoelectric to the Q complex, changes in the slope of the increase towards the R complex, changes in the absolute depth of the Q complex, changes in the absolute height of the R complex, changes in the absolute length of the ST complex, changes in the absolute length of the ST complex including the T complex, changes in the absolute length of the ST complex including the U complex, changes in the distance from the beginning of the P complex and the top of the P complex to the top of the R complex, changes in the slope of the distance from the beginning of the P complex and the top of the P complex to the top of the R complex, changes in the distance from the top of R complex to the end of the T complex, changes in the slope of the distance from the top of the R complex to the end of the T complex, and changes in the area under the triangle built of both the distance from the beginning of the P complex and the top of the P complex to the top of the R complex, as well as its corresponding slope, with an isoelectric line.

5. The system of claim 1, wherein the processor executes a mathematical algorithm to analyze, quantify, and combine the prognostic index of the changes in the electrocardiogram signal.

6. The system of claim 1, wherein the detection, analysis, and processing of the changes in at least one of the length, amplitude, slope, area, depth, and height of at least one of the P, Q, R, S, T, and U complex of the electrocardiogram signal is based at least in part on the Simpson's rule.

7. The system of claim 1, wherein the electrocardiogram signal is obtained non-invasively.

8. A processor-implemented method for treating a patient, comprising:
continuously obtaining, using a sensor, a high-resolution electrocardiogram signal at a frequency of greater than 250 Hz to about 1000 Hz as continuous high-resolution electrocardiogram data;
detecting, analyzing, and processing, by a processor using real-time processing, changes within a range of 10 to 30% in at least one of length, amplitude, slope, area, depth, and height of one or more of P, Q, R, S, T, and U complexes of the continuous electrocardiogram signal, including determining changes in an area under the curve of the QRS complex, and a change in the rise angle of the QRS complex, caused by the influence of physiological variables on each other to create a prognostic index;
analyzing, quantifying, and combining the prognostic index of the changes in the high frequency electrocardiogram signal at the frequency of greater than 250 Hz to about 1000 Hz to generate a fluid responsiveness prediction using real-time processing to continuously update the fluid responsiveness prediction; and
continuously displaying, on a display device, the fluid responsiveness prediction.

9. The method of claim 8, further comprising administrating fluid to a patient based on the fluid responsiveness prediction.

10. The method of claim 8, further comprising administrating medication to a patient based on the results of the fluid responsiveness prediction.

11. The method of claim 8, wherein the electrocardiogram signal is obtained using at least two sensors.

12. The method of claim 8, wherein the detection, analysis, and processing of the changes in at least one of the length, amplitude, slope, area, depth, and height of at least one of the P, Q, R, S, T, and U complex of the electrocardiogram signal is performed using a processor within a computer system.

13. The method of claim 12, wherein the detection, analysis, and processing of the changes in at least one of the length, amplitude, slope, area, depth, and height of at least one of the P, Q, R, S, T, and U complex of the electrocardiogram signal is based at least in part on the Simpson's rule.

14. The method of claim 8, wherein the analyzing, quantifying, and combining of the prognostic index of the changes in the electrocardiogram signal is performed using a processor within a computer system to execute a mathematical algorithm.

15. The method of claim 8, wherein the fluid responsiveness prediction is displayed using a display device.

16. The method of claim 8, wherein the prognostic index is based on at least two physiological variables.

17. The method of claim 16, wherein the physiological variables include at least two of heart rate, breathing, and vascular tone.

18. The method of claim 8, wherein the prognostic index depends on at least one of: changes in the absolute length of the P complex in a range of 10-25%, changes in the absolute amplitude of the P complex in a range of 10-30%, changes in the slope of the P complex in a range of 5-25%, changes in the area under the curve of the P complex in a range of 10-30%, changes in the PQ complex in a range of 15-35%, changes in the absolute length of the QRS complex, changes in the slope of the decrease from isoelectric to the Q complex, changes in the slope of the increase towards the R complex, changes in the absolute depth of the Q complex, changes in the absolute height of the R complex, changes in the absolute length of the ST complex, changes in the absolute length of the ST complex including the T complex, changes in the absolute length of the ST complex including the U complex, changes in the distance from the beginning of the P complex and the top of the P complex to the top of the R complex, changes in the slope of the distance from the beginning of the P complex and the top of the P complex to the top of the R complex, changes in the distance from the top of R complex to the end of the T complex, changes in the slope of the distance from the top of the R complex to the end of the T complex, and changes in the area under the triangle built of both the distance from the beginning of the P complex and the top of the P complex to the top of the R complex, as well as its corresponding slope, with an isoelectric line.

19. The method of claim 8, wherein the electrocardiogram signal is obtained non-invasively.

* * * * *